(12) United States Patent
Amoah et al.

(10) Patent No.: US 8,585,694 B2
(45) Date of Patent: Nov. 19, 2013

(54) ELECTROSURGICAL GENERATOR

(75) Inventors: Francis Amoah, Reading (GB); Wayne Williams, Penarth (GB)

(73) Assignee: Gyrus Medical Limited, Cardiff (GB)

( * ) Notice: Subject to any disclaimer, the term of this patent is extended or adjusted under 35 U.S.C. 154(b) by 769 days.

(21) Appl. No.: 12/662,808

(22) Filed: May 4, 2010

(65) Prior Publication Data

US 2010/0286685 A1 Nov. 11, 2010

Related U.S. Application Data

(60) Provisional application No. 61/213,197, filed on May 15, 2009.

(30) Foreign Application Priority Data

May 11, 2009 (GB) .................................. 0908067.2

(51) Int. Cl.
*A61B 18/14* (2006.01)
(52) U.S. Cl.
USPC .............................................. 606/34; 606/51
(58) Field of Classification Search
USPC .................................. 606/32–35, 41, 45–52
See application file for complete search history.

(56) References Cited

U.S. PATENT DOCUMENTS

| | | |
|---|---|---|
| 5,233,515 A | 8/1993 | Cosman |
| 5,423,810 A | 6/1995 | Goble et al. |
| 5,540,684 A | 7/1996 | Hassler, Jr. |
| 5,827,271 A | 10/1998 | Buysse et al. |
| 6,228,080 B1 | 5/2001 | Gines |
| 6,648,883 B2 | 11/2003 | Francischelli et al. |
| 6,730,080 B2 | 5/2004 | Harano et al. |
| 6,743,229 B2 | 6/2004 | Buysse et al. |
| 6,893,435 B2 | 5/2005 | Goble |
| 7,172,591 B2 | 2/2007 | Harano et al. |
| 2007/0016182 A1* | 1/2007 | Lipson et al. .................... 606/34 |
| 2007/0173804 A1* | 7/2007 | Wham et al. .................... 606/34 |
| 2010/0168572 A1* | 7/2010 | Sliwa et al. .................... 600/439 |
| 2010/0217258 A1* | 8/2010 | Floume et al. .................... 606/34 |

FOREIGN PATENT DOCUMENTS

| | | |
|---|---|---|
| WO | WO 02/36028 A1 | 5/2002 |
| WO | WO 02/071926 A2 | 9/2002 |
| WO | WO 03/070284 A2 | 8/2003 |

OTHER PUBLICATIONS

British Search Report issued in British Patent Application No. GB0908067.2, on Sep. 11, 2009.

* cited by examiner

*Primary Examiner* — Michael Peffley
(74) *Attorney, Agent, or Firm* — Oliff & Berridge, PLC

(57) ABSTRACT

An electrosurgical generator for coagulating tissue comprises a source of radio frequency (RF) energy, and at least a pair of output terminals for connection to a bipolar electrosurgical instrument adapted to contact tissue, the output terminals delivering RF energy from the source to the instrument such that the source delivers RF energy into tissue. The generator also includes boiling detection means for determining when the RF energy starts to cause the boiling of electrolytes within the tissue. A timer is adapted to determine when a predetermined period of time has elapsed since the boiling detection means has indicated the start of the boiling of electrolytes. An indication means gives an indication when the predetermined period of time has elapsed.

36 Claims, 3 Drawing Sheets

ELECTROSURGICAL GENERATOR

FIELD OF THE INVENTION

This invention relates to an electrosurgical generator for use in the sealing of tissue, particularly blood vessels such as large veins and arteries.

BACKGROUND OF THE INVENTION

The coagulation of tissue, particularly the sealing or occlusion of vessels such as veins and arteries is an important feature of many surgical interventions. There is a range of equipment, both mechanical and electrosurgical, for sealing or clamping vascular tissue. In the electrosurgical field, it is typical for a jawed instrument to grasp tissue and deliver a coagulating radio frequency (RF) current. Prior art patents such as U.S. Pat. No. 6,893,435, and U.S. Pat. No. 6,743,229 disclose examples of this type of system. The subject matter of U.S. Pat. No. 6,893,435 is hereby specifically incorporated in the present application by reference.

It is essential to apply the coagulating current signal for sufficient time to enable the tissue to be fully coagulated, but it is not desirable to continue to apply current excessively after the time that the tissue is coagulated. Excessive application of a coagulating waveform will produce desiccation of the tissue, and it may become adhered to the jaws of the instrument, resulting in a tearing of the tissue when the jaws are removed. There have been numerous attempts to predict when the coagulation process has been completed, and advise the user of the system to end the application of power to the tissue. Some systems automatically stop the supply of RF power after a certain criteria has been reached. Examples of these types of systems include U.S. Pat. Nos. 5,423,810, 5,540,684, 5,827,271, 6,228,080, 6,648,883, 6,730,080, and 7,172,591. However, due to the variation between different samples of tissue being coagulated, both in terms of thickness and composition, each of the above systems has its own limitations. The present invention attempts to provide an improvement to this type of system, capable of dealing with a wider range of different tissue types and circumstances.

SUMMARY OF THE INVENTION

Accordingly, an electrosurgical generator for coagulating tissue is provided comprising a source of radio frequency (RF) energy, and at least a pair of output terminals for connection to a bipolar electrosurgical instrument adapted to contact tissue, the output terminals delivering RF energy from the source to the instrument such that the source delivers RF energy into tissue, boiling detection means for determining when the RF energy starts to cause the boiling of electrolytes within the tissue, a timer adapted to determine when a predetermined period of time has elapsed since the boiling detection means has indicated the start of the boiling of electrolytes, and indication means for giving an indication when the predetermined period of time has elapsed.

The above electrosurgical generator is capable of detecting when the boiling of electrolytes within the tissue has commenced, and then supplying RF power for a predetermined time thereafter. During the predetermined time after the boiling of electrolytes has been detected, the generator preferably supplies RF power such as to maintain the temperature of the tissue in a predetermined temperature range. It is an aim of the present invention to maintain the tissue substantially at the temperature at which the boiling of electrolytes occurs, for the predetermined period of time. For this reason, the generator can be described as delivering a "time at temperature" output, i.e. raising the tissue to the temperature at which the boiling of electrolytes will occur, and then subsequently maintaining the tissue at that temperature for a predetermined period of time.

As can be seen above, the detection of the boiling of electrolytes is an important feature of this electrosurgical generator. Accordingly, the boiling detection means preferably comprises a controller monitoring one or more output parameters of the electrosurgical generator. The boiling detection means conveniently comprises a controller monitoring the output voltage or current such as to determine the impedance of the tissue. The impedance of the tissue is a useful indicator of whether the electrolytes within the tissue are starting to boil. Conveniently, the boiling detection means comprises a controller monitoring the output voltage or current such as to determine the rate of change of the impedance of the tissue. Alternatively or additionally, the boiling detection means comprises a controller monitoring the output power of the electrosurgical generator. In one convenient arrangement, the boiling detection means comprises a controller which uses a combination of output power and the rate of change of impedance to determine the start of the boiling of electrolytes within the tissue.

Conveniently, the boiling detection means uses the algorithm below in order to determine the start of the boiling of electrolytes within the tissue $$x_n = \left[ \frac{(Z_n - Z_{n-1}) \times 100}{Z_{init}} \times \frac{C}{\text{Power}} \right]$$

where $Z_n$ and $Z_{n-1}$ are successive impedance calculations, $Z_{init}$ is the initial impedance calculation, C is a constant dependent upon the instrument being used to perform the calculation, and Power is the output power of the electrosurgical generator. C is typically in the range of 100 to 300, more typically 150 to 250, and conceivably approximately 200. The value of C for any particular sealing instrument will typically be derived empirically, by observing traces of the impedance of the tissue during the application of RF power, and determining the onset of the boiling of electrolytes within the tissue. Alternatively, a value of 200 can be used in the above algorithm, with less accurate, but still generally effective results.

Conveniently, successive values of $x_n$ are summed, and the boiling detection means determines the start of the boiling of electrolytes when the sum exceeds a predetermined value. The boiling detection means conveniently uses the algorithm $$y_n = \sum_{n=1}^{n=5} |x_n|$$

to sum the values of $x_n$ and the boiling detection means determines the start of the boiling of electrolytes when exceeds a value of 150. By using the above algorithms, the onset of the boiling of electrolytes within the tissue can be detected, and the "time at temperature" period for the application of RF current established.

In one convenient arrangement, the indication means terminates the delivery of RF energy when the timer determines that the predetermined period of time has elapsed. This may be an optional feature within the generator, to take into account user preference. Some users may prefer the generator to have an automatic stop for the application of RF power, others may prefer merely an audible or visual indication, and to leave the ending of the process as a manual operation.

Either way, the user of the preferred generator has a prompt that the application of RF current is considered to be sufficient, as a prompt to end the application of RF energy. The term "indication" is here used in its broadest sense insofar as it may be no more than an electrical signal that is indicative of the elapsing of the predetermined period. It is not essential to provide an indication of this to the user, although this is preferred. The value for the predetermined period may be set manually, but conveniently the timer employs a predetermined period of time of between 0.5 and 5 seconds, typically between 0.75 and 3 seconds, and preferably between 1 and 2 seconds. In an optional arrangement, the indication means gives a second indication a further period after the timer determines that the predetermined period of time has elapsed. This acts as an indication to the user of how long to wait after the application of RF energy before opening the jaws of the instrument. This provides a further period during which the mechanical force on the tissue is maintained, but the tissue is allowed to cool. The provision of this further period has been found to be beneficial in producing effective tissue sealing without tearing when the jaws are opened. Typically, the indication means employs a further period of between 0.25 and 2 seconds, conveniently between 0.5 and 1 second.

According to a further aspect of the invention, an electrosurgical system for coagulating tissue is provided, comprising an electrosurgical generator for coagulating tissue, the electrosurgical generator comprising a source of radio frequency RF energy, and at least a pair of output terminals, an electrosurgical instrument electrically connected to the output terminals of the electrosurgical generator such that the electrosurgical instrument delivers RF energy into tissue, boiling detection means for determining when the RF energy starts to cause the boiling of electrolytes within the tissue, a timer adapted to determine when a predetermined period of time has elapsed since the boiling detection means has indicated the start of the boiling of electrolytes, and indication means for giving an indication when the predetermined period of time has elapsed. As mentioned previously, the electrosurgical instrument conveniently comprises a jawed instrument, the jaws being capable of grasping tissue therebetween.

The invention further resides in a method of coagulating tissue comprising the steps of
  i) grasping the tissue with an electrosurgical instrument,
  ii) applying RF energy to the tissue through the electrosurgical instrument, the RF energy being sufficient to induce the boiling of electrolytes within the tissue,
  iii) detecting the onset of boiling of the electrolytes within the tissue,
  iv) maintaining RF energy for a predetermined period of time from the detection of the onset of boiling, and
  v) giving an indication to the user of the electrosurgical instrument at the end of the predetermined period of time.

As mentioned previously, the indication to the user of the electrosurgical instrument is preferably a visual or audible signal. Alternatively or additionally, the indication to the user of the electrosurgical instrument is the automatic termination of the application of RF energy.

As mentioned previously, the aim of the present invention is to maintain the tissue substantially at the boiling point of the electrolytes within the tissue for a predetermined period of time. Accordingly, the RF energy is conveniently maintained for the predetermined period of time at substantially the same power level as was applied when the onset of boiling is detected. However, under certain circumstances, even though the power is not increased further, the temperature of the tissue can still be increasing during the predetermined period. Thus, according to an alternative arrangement, the RF energy is maintained for the predetermined period of time at a reduced power level as compared with the power level as was applied when the onset of boiling is detected. Typically, the power is reduced by between 5 and 20% as compared with the power level as was applied when the onset of boiling is detected. By "backing off" the power after the boiling of electrolytes is detected, the generator avoids overheating of the tissue and possible tissue damage caused by such overheating, as well as the tendency for tissue to become adhered to the electrodes of the instrument applying the RF energy.

As an alternative to maintaining the power level as described above, the RF energy is conceivably maintained for the predetermined period of time at substantially the same voltage level as was applied when the onset of boiling is detected. As before, the RF energy is alternatively maintained for the predetermined period of time at a reduced voltage level as compared with the voltage level as was applied when the onset of boiling is detected, in order to prevent overheating as previously described. Conveniently, the voltage is reduced by between 5 and 20% as compared with the voltage level as was applied when the onset of boiling is detected.

The invention will be described in more detail below, by way of example only, with reference to the accompanying drawings.

DETAILED DESCRIPTION OF THE PREFERRED EMBODIMENT OF THE INVENTION

Figure 1:
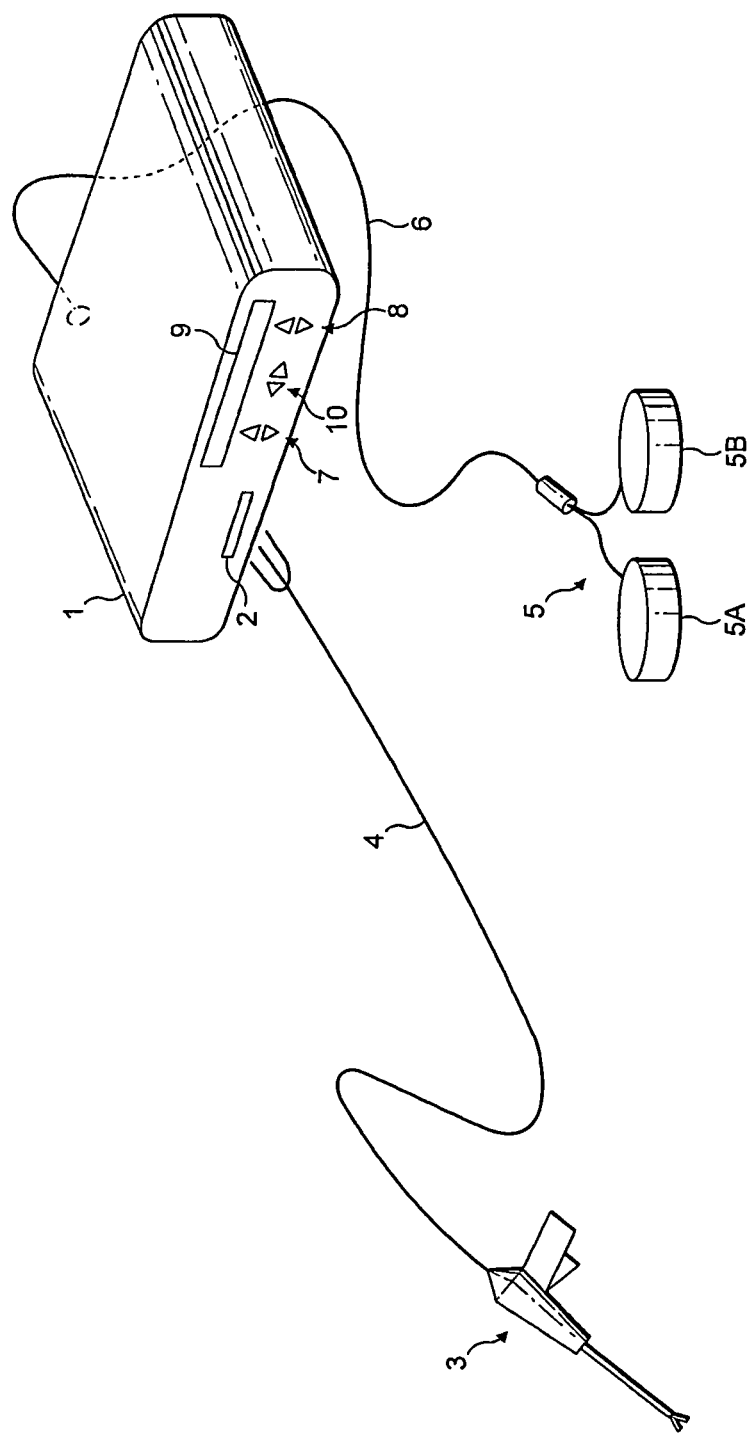
FIG. 1 is a schematic diagram of an electrosurgical system including a generator in accordance with the present invention.

Referring to FIG. 1, a generator 1 has an output socket 2 providing a radio frequency (RF) output for an instrument 3 via a connection cord 4. Activation of the generator 1 may be performed from the instrument 3 via a connection in the cord 4, or by means of a footswitch unit 5, as shown, connected to the rear of the generator by a footswitch connection cord 6. In the illustrated embodiment, the footswitch unit 5 has two footswitches 5A, 5B for selecting a coagulation mode and a cutting mode of the generator 1 respectively. The generator front panel has push buttons 7, 8 for respectively setting coagulation and cutting power levels, which are indicated in a display 9. Push buttons 10 are provided as an alternative means for selection between coagulation and cutting modes.

Figure 2A:
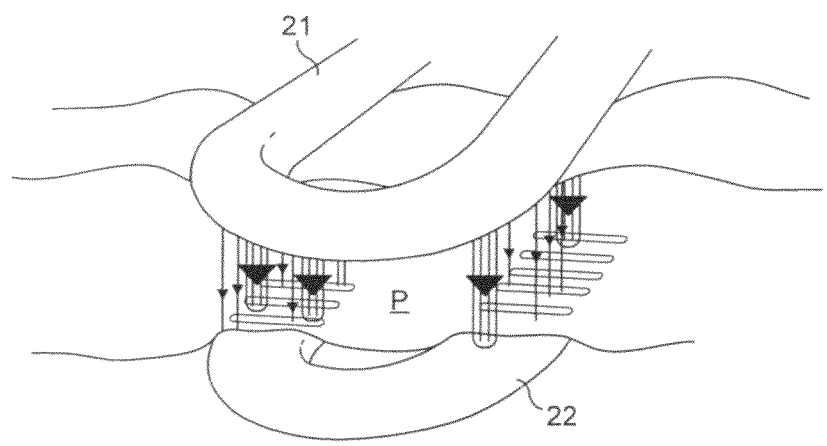
FIGS. 2a and 2b are enlarged schematic views of a part of the instrument shown in FIG. 1, shown in a first stage of operation.
Figure 2B:
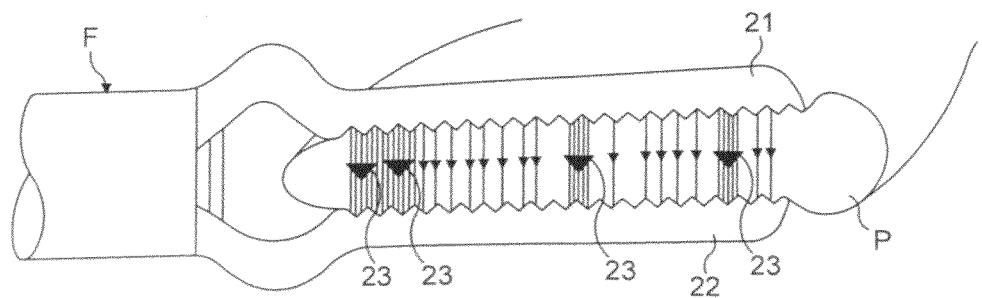

FIGS. 2a and 2b show a typical forceps device F, grasping a pedicle P of tissue between the jaws 21, 22 of the forceps F. These figures show different perspective views of the forceps F, respectively from the distal end thereof and from the side. The current density between the forceps jaws (electrodes) 21, 22 is variable over the tissue contact area creating zones of high current density, shown by the arrowhead symbols 23 in FIGS. 2a and 2b. The variations in impedances which may occur as a result of, amongst other things, the non-parallel closure of the forceps F and the non-uniform nature of the tissue, creates the zones 23 of high current density. The zones 23 of high current density create hot spots at the contact surfaces between the tissue and the forceps jaws 21, 22. The hot spots created in the zones 23 of high current density reduce the impedance of these zones even further compared to the other areas of the tissue. All the current from the output becomes concentrated in these hot spots which exhibit the phenomenon of current hogging. The RF energy supplied to the jaws 21, 22 is in the form of pulses, as described in the above-referenced U.S. Pat. No. 6,893,435. The zones of high current density are instantly created, as shown in FIGS. 2a and 2b, by the burst of bipolar RF energy. As has already been described, these zones of higher current density are more likely to be created in thinner tissue when the forceps jaws are closer together. This situation can be created by first grasping the tissue within the jaws, and preferably employing a ratchet feature on the forceps F so that the tissue is crushed and held at an optimal cross-section. Under these circumstances, when the first pulse is applied, the tissue in the zones of high current density reaches 100° C. virtually instantly.

Figure 3A:
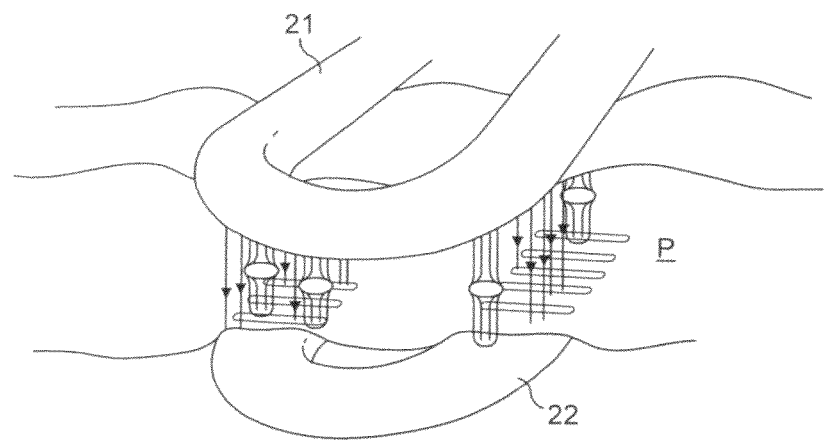
FIGS. 3a and 3b are enlarged schematic views of a part of the instrument shown in FIG. 1, shown in a further stage of operation.
Figure 3B:
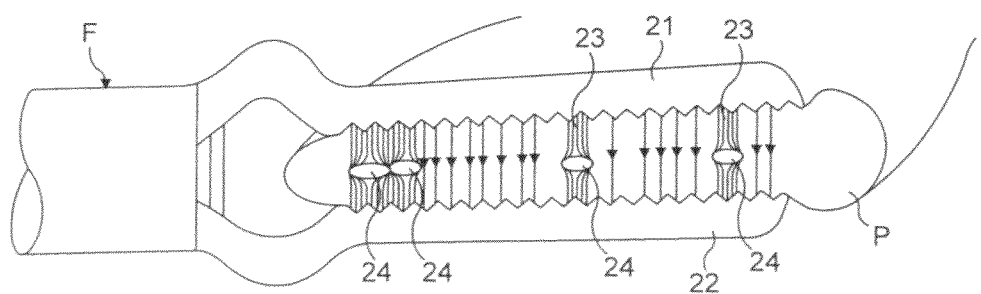

FIGS. 3a and 3b show how the power of the first pulse is dissipated in the centre of the tissue pedicle P in zones 23 of high current density, creating pockets 24 of water vapour (steam) in the intracellular and interstitial fluids. High current and high power is used to form the vapour pockets 24. The creation of the vapour pockets 24 produces two benefits: the vapour pockets 24 produce a high impedance barrier which prevents further current hogging, and the highest current densities occur around the lateral edges of the vapour pockets. Heat generation and coagulation start internally, within the tissue pedicle P, rather than in the external contact area between the tissue and the forceps jaws 21, 22.

The generator 1 (FIG. 1) may take the form shown in the diagram appearing as FIG. 14 in the above-referenced U.S. Pat. No. 6,893,435. That generator has a controller which receives signals representative of output voltage and current and controls energisation of a radio frequency oscillator acting as the radio frequency source. In the present generator, the controller is programmed to detect electrolyte boiling and to run a timer (typically in software) to count out a predetermined period of time from the detected start of boiling.

The generator 1 takes readings of the output voltage every 10 ms and uses these readings together with the power setting of the generator to calculate the impedance across the jaws 21, 22. These sequential impedance values are applied to the algorithm below as follows:

$$x_n = \left[\frac{(Z_n - Z_{n-1}) \times 100}{Z_{init}} \times \frac{200}{\text{Power}}\right]$$

where $Z_n$ and $Z_{n-1}$ are successive impedance calculations, $Z_{init}$ is the initial impedance calculation, and Power is the output power of the electrosurgical generator. The generator 1 sums successive values of $x_n$ and calculates when the sum exceeds a predetermined value. The generator 1 uses the algorithm $$y_n = \sum_{n=1}^{n=5} |x_n|$$

to sum the values of $x_n$ and calculates when $y_n$ exceeds a value of 150. When $y_n$ exceeds 150, the generator determines that the boiling of electrolytes within the tissue has started and that pockets 24 of water vapour (steam) in the intracellular and interstitial fluids are starting to be created as described previously with reference to FIGS. 3a and 3b. At this point the generator 1 starts the timer which counts out a predetermined period of time, in this case 2 seconds, before indicating on the display 9 that the coagulation is complete and sounding an audible tone. The generator has an optional setting which, if activated, discontinues or substantially reduces the supply of RF energy at this time.

The timer is then reset by the generator and counts out a further period of 1.5 seconds, after which time a further message is displayed on display 9 and a further audible tone is sounded, indicating to the user that it is now time to open the jaws 21, 22 and release the tissue therebetween. By operating in this way, the generator 1 ensures that adequate coagulation of the tissue pedicle P has occurred, while reducing the risk of sticking due to desiccation of the tissue.

What is claimed is:

1. An electrosurgical generator for coagulating tissue comprising:
   a source of radio frequency RF energy;
   at least a pair of output terminals for connection to a bipolar electrosurgical instrument adapted to contact tissue, the output terminals delivering RF energy from the source to the instrument such that the source delivers the RF energy into the tissue,
   boiling detection means for determining when the RF energy starts to cause a boiling of electrolytes within the tissue,
   a timer adapted to determine when a predetermined period of time has elapsed since the boiling detection means has indicated the start of the boiling of electrolytes, and
   indication means for giving an indication when the predetermined period of time has elapsed, wherein
   the predetermined period of time is determined prior to the delivery of the RF energy.

2. An electrosurgical generator according to claim 1, wherein the boiling detection means comprises a controller arranged to monitor at least one or more output parameter of the electrosurgical generator.

3. An electrosurgical generator according to claim 2, wherein the boiling detection means comprises a controller arranged to monitor at least one of an output voltage and an output current in order to determine a tissue impedance.

4. An electrosurgical generator according to claim 3, wherein the boiling detection means comprises a controller arranged to monitor at least one of an output voltage and an output current in order to determine a rate of change of the impedance of the tissue.

5. An electrosurgical generator according to claim 2, wherein the boiling detection means comprises a controller arranged to monitor an output power of the electrosurgical generator.

6. An electrosurgical generator according to claim 5, wherein the boiling detection means comprises a controller arranged to monitor at least one of an output voltage and an output current in order to determine a rate of change of tissue impedance and to use a combination of output power and the rate of change of impedance to determine the start of the boiling of electrolytes within the tissue.

7. An electrosurgical generator according to claim 6, wherein the boiling detection means is arranged to use an algorithm below in order to determine the start of the boiling of electrolytes within the tissue $$x_n = \left[\frac{(Z_n - Z_{n-1}) \times 100}{Z_{init}} \times \frac{C}{\text{Power}}\right]$$

where $Z_n$ and $Z_{n-1}$ are successive impedance calculations, $Z_{init}$ is an initial impedance calculation, C is a constant, and Power is the output power of the electrosurgical generator.

8. An electrosurgical generator according to claim 7, arranged such that successive values of $x_n$ are summed and the boiling detection means determines the start of the boiling of electrolytes when the sum exceeds a predetermined value.

9. An electrosurgical generator according to claim 8, wherein the boiling detection means uses an algorithm $$y_n = \sum_{n=1}^{n=5} |x_n|$$

to sum the values of $x_n$ and
the boiling detection means determines the start of the boiling of electrolytes when $y_n$ exceeds a value of 150.

10. An electrosurgical generator according to claim 1, wherein the indication means is arranged to terminate the delivery of RF energy when the timer determines that the predetermined period of time has elapsed.

11. An electrosurgical generator according to claim 1, wherein the timer employs a predetermined period of time of between 0.5 and 5 seconds.

12. An electrosurgical generator according to claim 11, wherein the timer employs a predetermined period of time of between 0.75 and 3 seconds.

13. An electrosurgical generator according to claim 12, wherein the timer employs a predetermined period of time of between 1 and 2 seconds.

14. An electrosurgical generator according to claim 1, wherein the indication means is arranged to give a second indication of a further period after the timer determines that the predetermined period of time has elapsed.

15. An electrosurgical generator according to claim 14, wherein the indication means employs a further period of between 0.25 and 2 seconds.

16. An electrosurgical generator according to claim 15, wherein the indication means employs a further period of between 0.5 and 1 second.

17. An electrosurgical system for coagulating tissue comprising
an electrosurgical generator for coagulating tissue, the electrosurgical generator comprising
a source of radio frequency (RF) energy, and
at least a pair of output terminals;
an electrosurgical instrument electrically connected to the output terminals of the electrosurgical generator to allow the electrosurgical instrument to deliver RF energy into the tissue,
boiling detection means for determining when the RF energy starts to cause a boiling of electrolytes within the tissue,
a timer adapted to determine when a predetermined period of time has elapsed since the boiling detection means has indicated the start of the boiling of electrolytes, and
indication means for giving an indication when the predetermined period of time has elapsed, wherein
the predetermined period of time is determined prior to the delivery of the RF energy.

18. An electrosurgical system according to claim 17, wherein the electrosurgical instrument includes jaws capable of grasping tissue therebetween.

19. An electrosurgical system according to claim 17, wherein the boiling detection means comprises
a controller forming part of the generator and arranged to monitor at least one output parameter of the generator.

20. An electrosurgical system according to claim 17, wherein the indication means of the electrosurgical generator is arranged to terminate the delivery of RF energy when the timer determines that the predetermined period of time has elapsed.

21. An electrosurgical system according to claim 17, wherein the indication means of the electrosurgical generator is arranged to give a second indication of a further period after the timer determines that the predetermined period of time has elapsed.

22. A method of coagulating tissue comprising the steps of:
i) grasping the tissue with an electrosurgical instrument,
ii) applying RF energy to the tissue through the electrosurgical instrument, the RF energy being sufficient to induce a boiling of electrolytes within the tissue,
iii) detecting an onset of boiling of the electrolytes within the tissue,
iv) maintaining the RF energy for a predetermined period of time from the detection of the onset of boiling, and
v) giving an indication to a user of the electrosurgical instrument at an end of the predetermined period of time, wherein the predetermined period of time is determined prior to the delivery of the RF energy.

23. A method according to claim 22, wherein the indication to the user of the electrosurgical instrument is at least one of a visual and an audible signal.

24. A method according to claim 22, wherein the indication to the user of the electrosurgical instrument is an automatic termination of the application of the RF energy.

25. A method according to claim 22, wherein the RF energy is maintained for the predetermined period of time at substantially a same power level as applied when the onset of boiling is detected.

26. A method according to claim 22, wherein the RF energy is maintained for the predetermined period of time at a reduced power level compared with a power level being applied when the onset of boiling is detected.

27. A method according to claim 26, wherein the power level is reduced by between 5 and 20% compared with the power level being applied when the onset of boiling is detected.

28. A method according to claim 22, wherein the RF energy is maintained for the predetermined period of time at substantially a same voltage level as applied when the onset of boiling is detected.

29. A method according to claim 22, wherein the RF energy is maintained for the predetermined period of time at a reduced voltage level compared with a voltage level being applied when the onset of boiling is detected.

30. A method according to claim 29, wherein the voltage level is reduced by between 5 and 20% compared with the voltage level being applied when the onset of boiling is detected.

31. A method according to claim 22, wherein the predetermined period of time is between 0.5 and 5 seconds.

32. A method according to claim 31, wherein the predetermined period of time is between 0.75 and 3 seconds.

33. A method according to claim 32, wherein the predetermined period of time is between 1 and 2 seconds.

34. A method according to claim 22, further comprising an additional step of providing a second indication of a further period after the end of the predetermined period of time.

35. A method according to claim 34, wherein the further period is between 0.25 and 2 seconds.

36. A method according to claim 35, wherein the further period is between 0.5 and 1 second.

* * * * *